United States Patent
Babkin et al.

(10) Patent No.: US 9,345,527 B2
(45) Date of Patent: *May 24, 2016

(54) METHOD AND SYSTEM FOR CRYOABLATION TREATMENT

(75) Inventors: Alexei V. Babkin, Albuquerque, NM (US); Peter J. Littrup, Bloomfield Hills, MI (US); William J. Nydam, Rancho Santa Fe, CA (US)

(73) Assignee: CRYOMEDIX, LLC, San Diego ( * ) Notice: Subject to any disclaimer, the term of this patent is extended or adjusted under 35 U.S.C. 154(b) by 1232 days.

This patent is subject to a terminal disclaimer.

(21) Appl. No.: 13/292,967

(22) Filed: Nov. 9, 2011

(65) Prior Publication Data

US 2012/0053575 A1    Mar. 1, 2012

Related U.S. Application Data

(62) Division of application No. 12/425,938, filed on Apr. 17, 2009, now Pat. No. 8,814,850.

(60) Provisional application No. 61/047,496, filed on Apr. 24, 2008.

(51) Int. Cl.
*A61B 18/18* (2006.01)
*A61B 18/02* (2006.01)
*A61B 18/00* (2006.01)

(52) U.S. Cl.
CPC ....... *A61B 18/02* (2013.01); *A61B 2018/00041* (2013.01); *A61B 2018/0262* (2013.01)

(58) Field of Classification Search
CPC .......... A61B 18/02; A61B 2018/0262; A61B 2018/00041
See application file for complete search history.

(56) References Cited

U.S. PATENT DOCUMENTS

| | | | | |
|---|---|---|---|---|
| 5,281,215 A * | 1/1994 | Milder | .......... | A61B 18/02 606/20 |
| 5,334,181 A * | 8/1994 | Rubinsky | .......... | A61B 18/02 606/20 |
| 7,318,821 B2 * | 1/2008 | Lalonde | .......... | A61B 18/02 606/21 |

* cited by examiner

*Primary Examiner* — Michael Peffley
*Assistant Examiner* — Amanda Zink
(74) *Attorney, Agent, or Firm* — Nydegger & Associates

(57) ABSTRACT

A system and a method for its use are provided to cool a cryotip at the distal end of a probe for a cryosurgical procedure. In particular, the cryotip is cooled by a liquid refrigerant to cryogenic temperatures in order to perform a cryosurgical procedure on biological tissue. The system is closed-loop, and during transit of the liquid refrigerant through the entire system, the liquid refrigerant always remains in a liquid state at a relatively low pressure.

3 Claims, 2 Drawing Sheets

METHOD AND SYSTEM FOR CRYOABLATION TREATMENT

This application is a divisional of application Ser. No. 12/425,938, filed Apr. 17, 2009, now U.S. Pat No. 8,814,850, issued Aug. 26, 2014. Application Ser. No. 12/425,938 claims the benefit of U.S. Provisional Patent Application Ser. No. 61/047,496, filed Apr. 24, 2008. The contents of application Ser. Nos. 12/425,938 and 61/047,496 are incorporated herein by reference.

FIELD OF THE INVENTION

The present invention pertains generally to systems and methods for performing a cryosurgical procedure. More particularly, the present invention pertains to systems and methods that use a probe having a cryotip for cooling biological tissues to cryogenic temperatures. The present invention is particularly, but not exclusively, useful as a closed-loop system wherein a liquid refrigerant remains in a liquid state as it is cycled through the system between its source and the cryotip of a probe.

BACKGROUND OF THE INVENTION

A probe that is to be used for cryosurgery must be designed with an optimally small shape and size to achieve selective cooling of biological tissues. The cryosurgical system must also be designed to provide reliable cooling of the part of the cryoprobe (i.e. the cryotip) that will be in direct thermal contact with the target biological tissue to be treated.

For many cryogenic treatment applications, temperatures below −90° C. are desirable, and some known cryosurgical systems use liquid refrigerants such as nitrogen, argon, nitrous oxide, carbon dioxide, various hydro/fluorocarbons, and others. Liquid nitrogen has a very desirable low temperature of approximately −200° C., but when it is introduced into the freezing zone of the cryoprobe, where it is in thermal contact with surrounding warm biological tissues, its temperature increases above the boiling temperature (−196° C.). Thus, it evaporates and expands several hundred-fold in volume at atmospheric pressure, and rapidly absorbs heat from the probe tip. This enormous increase in volume results in a "vapor lock" effect when the mini-needle of the cryoprobe gets "clogged" by the gaseous nitrogen. Additionally, in these systems the gaseous nitrogen is typically rejected directly to the atmosphere. This produces a cloud of condensate upon exposure to the atmospheric moisture in the operating room and requires frequent refilling or replacement of the liquid nitrogen storage tank.

Several liquid nitrogen systems have been proposed. For example, improved cryosurgical systems and methods for supplying liquid nitrogen to a probe tip are disclosed in U.S. Pat. Nos. 5,520,682, and 7,192,426, both of which issued to Baust et al. Further, a system for the direct and/or indirect delivery of liquid nitrogen to a probe tip is disclosed in U.S. Pat. No. 5,334,181 which issued to Rubinsky et al. For these and other similar type systems, cryosurgical practice shows that current cooling systems and methods that are based on the use of liquid nitrogen as a means to cool a miniature probe tip are not practicably feasible. In large part, this is due to the rapid transition of the liquid nitrogen into the gaseous state followed by an inevitable "vapor lock."

Nitrous oxide and carbon dioxide cooling systems typically achieve cooling when pressurized gases are expanded through a Joule-Thomson expansion element such as a small orifice, throttle, or other type of flow construction that is disposed at the end tip of the cryoprobe. For example, a typical nitrous oxide system pressurizes the gas to about 5 to 5.5 MPa to reach a temperature of no lower than about −85 to −65° C. at a pressure of about 0.1 MPa. For carbon dioxide, the temperature of about −76° C. at the same pressure of 0.1 MPa is achieved with an initial pressure of about 5.5 MPa. Nitrous oxide and carbon dioxide cooling systems, however, are not able to achieve the temperature and cooling power provided by liquid nitrogen systems. On the other hand, nitrous oxide and carbon dioxide cooling systems have some advantages because the inlet of high pressurized gas at a room temperature, when it reaches the Joule-Thomson throttling component or other expansion device at the probe tip, excludes the need for thermal insulation of the system. However, because of an insufficiently low operating temperature combined with relatively high initial pressure, cryosurgical applications are strictly limited. Additionally, the Joule-Thomson system typically uses a heat exchanger to cool the incoming high pressure gas with the outgoing expanded gas in order to achieve the necessary drop in temperature by expanding compressed gas. Stated differently, these heat exchanger systems are not compatible with the desired miniature size of probe tips that must be less than at least 3 mm in diameter.

Several mixed gas refrigeration systems (e.g. Joule-Thompson systems) have been proposed for performing cryosurgical procedures. In particular, U.S. Pat. Nos. 5,787,715, 5,956,958, and 6,530,234, all of which issued to Dobak, Ill. et al., disclose cryogenic procedures using devices having mixed gas refrigeration systems. Other systems wherein a refrigerant transitions from a liquid to a gas (e.g. a Joule-Thomson effect) include systems disclosed in U.S. Pat. No. 6,074,572 which issued to Li et al. and U.S. Pat. No. 6,981,382 which issued to Lentz et al.

In review, systems using liquid nitrogen as a means to cool a miniature probe tip are subject to "vapor lock." On the other hand, systems that use highly pressurized gas mixtures in order to achieve the Joule-Thomson effect cannot provide operating temperatures lower than about −90° C. Thus, they are not desirable for many cryosurgical procedures.

In light of the above, an object of the present invention is to provide a closed-loop system for performing a cryosurgical procedure with a cryoprobe that maintains a liquid refrigerant in its liquid state as it transits through the system. More specifically, it is an object of the present invention to provide a system and method for performing a cryoablation treatment that employs non-evaporative liquid refrigerants at a low pressure (e.g. 0.3 MPa), and at a low temperature (e.g. less than −100° C.). It is another object of the present invention to provide a cryoablation system that can be customized to use any one of several different liquid refrigerants. Still another object of the present invention is to provide a cryoablation system that incorporates a means for removing frozen biological tissue that may adhere to the cryoprobe during a cryosurgical treatment. It is also another object of the present invention to provide a cryoablation system that is easy to use, is relatively simple to manufacture and is comparatively cost effective.

SUMMARY OF THE INVENTION

A system and method for performing a procedure for the cryosurgical treatment of biological tissue includes a probe (i.e. a cryoprobe) and a liquid refrigerant for cooling the tip of the probe for the procedure. The system is closed-loop and, importantly, the liquid refrigerant always remains in a liquid state as it is circulated through the system. As envisioned for the present invention, low temperatures (e.g. less than −100° C.) and low pressures (e.g. as low as 0.3 MPa) are achievable at the tip of the cryoprobe.

Structurally, the cryoablation system of the present invention includes a container for holding a liquid refrigerant. Depending on the particular liquid refrigerant being used, the liquid refrigerant is held in the container, as a liquid, at a base pressure "$P_B$" and at a temperature "$T_R$". Specifically, $T_R$ is substantially the same or slightly cooler than the environmental temperature where the container is located. For purposes of the present invention the liquid refrigerant is preferably selected from a group of refrigerants including R124, R218, R290, R1270 and R600A.

In addition to the liquid refrigerant container, the system also includes a cryoprobe. In detail, this cryoprobe includes a hollow, substantially tubular-shaped vacuum shell having a proximal end and a distal end. A cryotip that is formed with a liquid-tight chamber is attached to the distal end of the vacuum shell. And, a cold inlet line extends through the vacuum shell from its proximal end to its distal end to establish fluid communication with the chamber of the cryotip. Similarly, a return line extends proximally from the chamber of the cryotip, and back through the vacuum shell, to establish fluid communication between the chamber of the cryotip and the proximal end of the cryoprobe. Preferably, the outside diameters of the cryotip and of the vacuum shell are less than approximately 3 mm. As intended for the present invention, the vacuum shell is provided to thermally isolate the cold inlet line and the return line from contact with surrounding tissue while the cryoprobe is positioned for a procedure. Further, a turbulator can be positioned in the chamber of the cryotip to assist in the movement of liquid refrigerant through the cryoprobe.

Positioned in order along the cold inlet line, between the liquid refrigerant container and the cryoprobe, are a liquid pump and a refrigerator. For the present invention, the liquid pump is used to initially move liquid refrigerant from the container and subsequently through the system at an elevated operational pressure $P_{opn}$. The refrigerator is positioned as mentioned above to receive liquid refrigerant from the pump at the operational pressure $P_{opn}$, and to then cool it to a temperature $T_{min}$. Exemplary values for $T_{min}$ and $P_{opn}$ are, respectively, a temperature less than about −100° C., and a pressure in a range between approximately 0.3 MPa and approximately 5.0 MPa. Thus, the liquid refrigerant enters the cold inlet line for transfer to the chamber of the cryotip at the temperature $T_{min}$ and the pressure $P_{opn}$.

In a preferred embodiment of the present invention, the system provides a means for separating the cryotip from target tissue when there is an adhesion. For this purpose, the cold inlet line may also include a heater for receiving a portion of the liquid refrigerant from the pump, and for heating the portion of liquid refrigerant. The heated, or warmed, liquid refrigerant is then directly transferred to the cryoprobe for the purpose of removing any adhesion of biological tissue that may have occurred during the cryosurgical treatment. In this operation, the temperature of the heated liquid refrigerant can be controlled. More specifically, the system includes a first slide valve that is used for controlling the flow of liquid refrigerant from the pump to the refrigerator. There is also a second slide valve for controlling the flow of liquid refrigerant from the pump to the heater. The operation of the first and second slide valves can then be coordinated to mix liquid refrigerant from the heater with liquid refrigerant from the refrigerator to establish a predetermined temperature $T_P$ for liquid refrigerant in the cryoprobe that will remove the adhesion. To do this, of course, $T_P$ needs to be greater than $T_R$.

Further, in the preferred embodiment of the present invention, the refrigerator will include a pressure vessel for holding a liquid cryogen. A portion of the cold inlet line that connects the container in fluid communication with the cryoprobe will then be coiled and submerged in the liquid cryogen. For the present invention, the liquid cryogen is preferably liquid nitrogen having a temperature in a range between −180° C. and −150° C. at a pressure in a range between 0.5 and 3.0 MPa, that will cool the liquid refrigerant to $T_{min}$.

In the return line, a heat exchanger and a check valve are positioned between the cryoprobe and the container. Functionally, this heat exchanger is positioned in the return line to heat the liquid refrigerant to $T_R$. And, the check valve is positioned in the return line to reduce pressure on the liquid refrigerant to $P_B$. Thus, the liquid refrigerant is returned to the container substantially at the temperature $T_R$, at the pressure $P_B$.

In an operation of the cryosurgical probe of the present invention, a liquid refrigerant is initially held in a container, as a liquid, at a predetermined temperature and pressure ($T_R$ and $P_B$). The liquid pump then pressurizes the liquid refrigerant to an operational pressure ($P_{opn}$) while the liquid refrigerant remains substantially at the temperature ($T_R$). Next, the refrigerator lowers the temperature of the liquid refrigerant from ($T_R$) to ($T_{min}$). The chilled and pressurized liquid refrigerant is then transferred through the vacuum shell to the cryotip where it is used for a cryosurgical procedure ($T_{min}$ and $P_{opn}$).

Once the liquid refrigerant has passed through the cryotip, it is warmed by a heat exchanger to the predetermined temperature ($T_R$). Additionally, a check valve reduces pressure on the liquid refrigerant to ($P_B$). The purpose here is twofold. For one, it insures that the refrigerant remains in its liquid phase through the cryotip and, thus, the system. For another, the liquid refrigerant can then be returned to the container at the initial temperature and pressure ($T_R$ and $P_B$) for recycling.

In an alternate embodiment of the cryoprobe, as noted above, the liquid refrigerant can be heated at the conclusion of a cryosurgical procedure to remove the cryotip of the probe from any adhesion it may have established with biological tissue. More specifically, this intermediate heating will take the liquid refrigerant up to a temperature ($T_P$) in the cryotip for removal of the adhesion therefrom. Additionally, if the refrigerant's temperature in this procedure is maintained above 60° C. it can be used to produce local tissue coagulation that eliminates bleeding. In detail, this heating will be caused by liquid refrigerant that is heated as it bypasses the refrigerator, but before it is introduced into the cryotip. The liquid refrigerant can then be subsequently cooled to $T_R$ as disclosed above.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
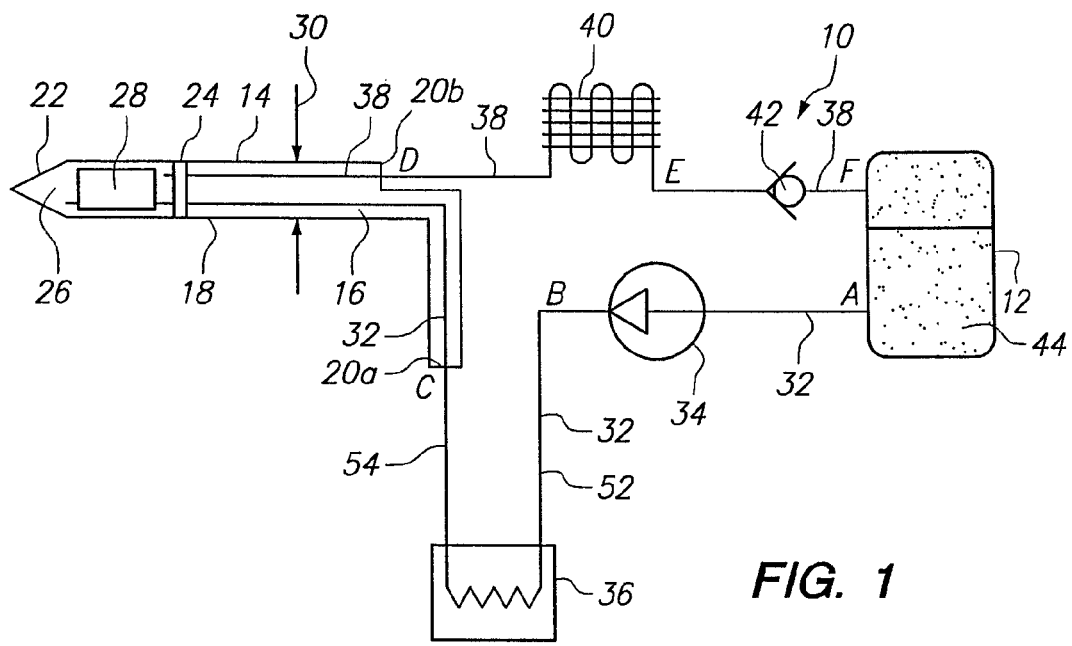
FIG. 1 is a schematic drawing of a cryoprobe system in accordance with the present invention.

Referring initially to FIG. 1, a system for performing a cryosurgical procedure in accordance with the present invention is shown and is generally designated 10. As shown, the system 10 essentially includes a liquid container 12 and a cryoprobe 14. In detail, the cryoprobe 14 includes a substantially tubular shaped vacuum shell 16 having a distal end 18 and a proximal end 20. For purposes to be disclosed in greater detail below, the proximal end 20 may be bifurcated into separate proximal ends 20a and 20b. In any event, the cryoprobe 14 will also include a cryotip 22 that is affixed to a plug 24 at the distal end 18 of the vacuum shell 16. Structurally, the cryotip 22 is formed with a liquid-tight chamber 26, and a turbulator 28 may be positioned inside the liquid-tight chamber 26. As indicated in FIG. 1, the outside diameter 30 of the cryoprobe 14 is substantially the same for both the vacuum shell 16 and the cryotip 22 and is, preferably, less than 3 mm.

FIG. 1 also shows that the system 10 includes a cold inlet line 32 that extends from the liquid container 12 for fluid communication with the liquid-tight chamber 26 of the cryotip 22. Integrated into the cold inlet line 32 between the container 12 and the proximal end 20a of the cryoprobe 14 are a liquid pump 34 and a refrigerator 36. Further, FIG. 1 shows that the system 10 includes a return line 38 that extends from the fluid-tight chamber 26 of the cryotip 22 through the proximal end 20b of the vacuum shell 16 for fluid communication with the container 12. Importantly, as emphasized by the exaggerated bifurcation of proximal ends 20a and 20b of the vacuum shell 16 shown in FIG. 1, the cold inlet line 32 and the return line 38 need to be thermally isolated from each other. The plug 24 mentioned above is provided to help accomplish this. Specifically, the plug 24 is located between the liquid-tight chamber 26 and the vacuum shell 16 to contain the liquid refrigerant 44 inside the liquid-tight chamber 26. Thus, the interior of vacuum shell 16 is separated from the cryotip 22 to thereby thermally insolate the cold inlet line 32 and the return line 38 from the liquid-tight chamber 26. Further, the vacuum in the vacuum shell 16 thermally isolates the cold inlet line 32 from the return line 38 inside the vacuum shell 16.

As intended for the system 10 of the present invention, a liquid refrigerant 44 remains in its liquid state at all times during an operational cycle. Further, it is important that the liquid refrigerant 44 be capable of attaining a temperature below approximately −100° C., at a relatively low pressure (e.g. in a range between about 0.3 MPa and 1.5 MPa, as it applies to R124 refrigerant). Several commercially available liquid refrigerants 44 have this capability and the preferred refrigerants 44 for use with the present invention are set forth in the TABLE below.

TABLE

| Refrigerant | Chemical formula | Molecular mass (kg/mol) | Normal freezing point (° C.) | Normal boiling point (° C.) |
|---|---|---|---|---|
| R124 | $C_2HClF_4$ | 136.5 | −199 | −12.1 |
| R218 | $C_3F_8$ | 188.02 | −150 | −36.7 |
| R290 | $C_3H_8$ | 44.1 | −183 | −88.6 |
| R1270 | $C_3H_6$ | 42.08 | −185 | −47.7 |
| R600A | $i-C_4H_{10}$ | 58.12 | −159.5 | −11.8 |

Importantly, the various liquid refrigerants 44 set forth in the above TABLE can be used selectively. Specifically, depending on the viscosity and temperature/pressure parameters of a liquid refrigerant 44 selected from the above TABLE, the system 10 can be effectively customized for a particular cryosurgical procedure.

Figure 2:
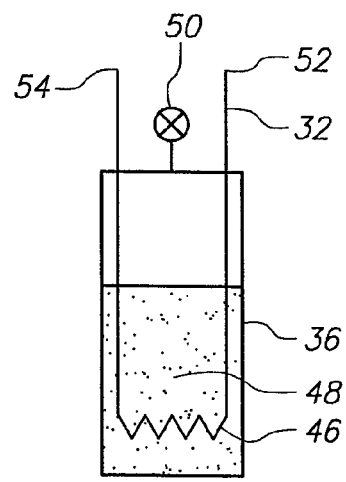
FIG. 2 is an alternate embodiment of a refrigerator for use with the cryoprobe system.

A preferred embodiment of the refrigerator 36 is shown in FIG. 2. There it will be seen that the cold inlet line 32 is formed with a coil 46 that is immersed in a liquid cryogen 48, such as liquid nitrogen. In this case, the liquid cryogen 48 is held in the refrigerator 36 at a temperature in a range between −180° C. and −150° C. at a pressure in a range between 0.5 and 3.0 MPa. Further, for this preferred embodiment of the refrigerator 36, a relief valve 50 is provided to help control the conditions for holding the liquid cryogen 48 as it may boil in the refrigerator 36. As will be appreciated by cross-referencing FIG. 2 with FIG. 1, the refrigerator 36 shown in FIG. 2 is incorporated into the system 10 by connections with the cold inlet line 32 at respective points 52 and 54.

Figure 3:
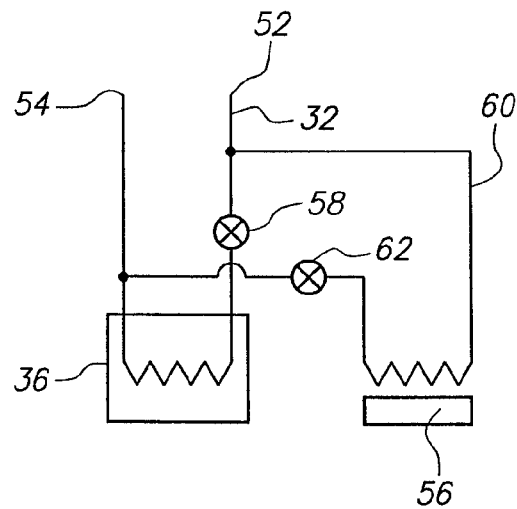
FIG. 3 is yet another alternate embodiment of a refrigerator for use with the cryoprobe system shown in combination with a heater for use in releasing the cryotip of the cryoprobe system from biological tissue after completion of a cryosurgical procedure.

An alternate embodiment of the cold inlet return line 32 is shown in FIG. 3. There, in addition to the refrigerator 36, it is seen that the cold inlet line 32 of the system 10 may incorporate a heat exchanger 56. In this embodiment, a slide valve 58 can be used to divert liquid refrigerant 44 flowing from the container 12 around the refrigerator 36 via a by-pass line 60. At the same time, a slide valve 62 can be manipulated to control the flow of liquid refrigerant 44 to the refrigerator 36. Thus, in essence, the refrigerator 36 can be completely, or partially, by-passed. The purpose here is to warm the refrigerant 44 for removal (detachment) of the cryotip 22 from any adhesion with biological tissue it may have established. This is accomplished by a concerted and coordinated use of the slide valves 58 and 62. Similar to the connections disclosed above for refrigerator 36 in FIG. 2, the embodiment of refrigerator 36 shown in FIG. 3 is incorporated into the system 10 by connections with the cold inlet line 32 at respective points 52 and 54.

Operation

Figure 4:
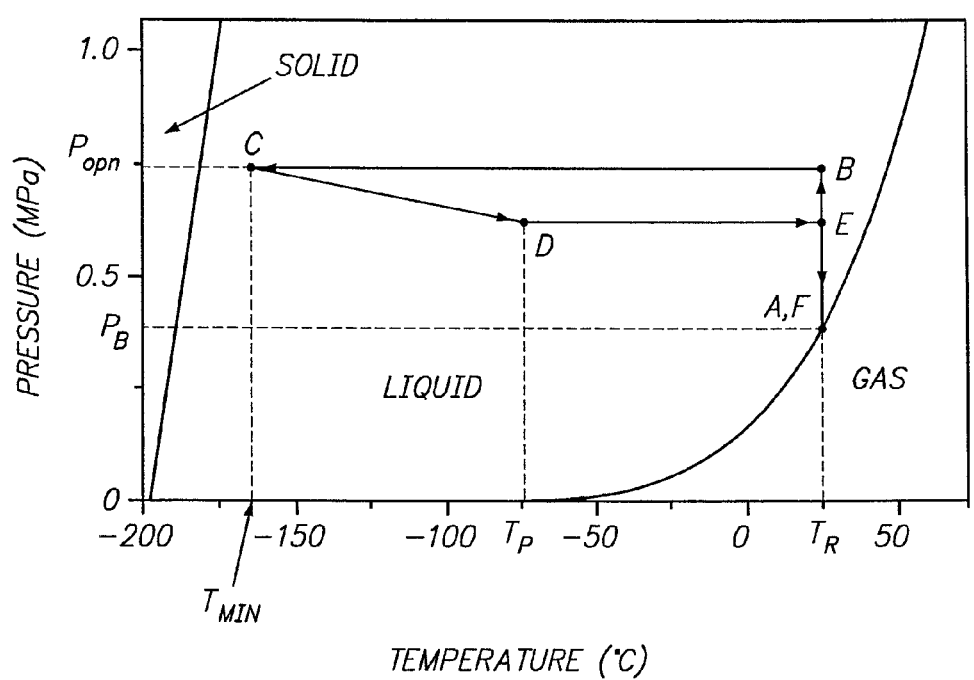
FIG. 4 is a phase diagram for an exemplary liquid refrigerant showing pressure and temperature changes of the liquid refrigerant during an operational cycle of the cryoprobe system using R124 refrigerant.

An operation of the system 10 of the present invention will be best appreciated by referring to FIG. 4, with cross-reference back to FIG. 1. For purposes of cross-referencing FIG. 4 with FIG. 1, a capital letter on the phase diagram (FIG. 4) corresponds to temperature and pressure conditions for liquid refrigerant 44 at the point indicated by the same capital letter shown on the system 10 (FIG. 1). For example, the capital letter "A" shown on the phase diagram in FIG. 4 indicates a temperature and pressure for the liquid refrigerant 44 that will be manifested at the location "A" shown on the system 10 in FIG. 1. In overview, the operation of system 10 involves a closed-loop manipulation of the liquid refrigerant 44 wherein it is continuously recycled through the system 10. Importantly, the liquid refrigerant 44 remains in its liquid state throughout each entire cycle.

To begin, a liquid refrigerant 44 is selected (see TABLE), and is held in a container 12 at a temperature $T_R$ (i.e. an environmental temperature of the system 10) and a pressure $P_B$. This corresponds to the point A shown in FIG. 4 where liquid refrigerant 44 is in its liquid state as it is introduced into the cold inlet line 32 (see FIG. 1). After the liquid refrigerant 44 leaves the container 12, the liquid pump 34 increases pressure on the liquid refrigerant 44. This pressure increase is accomplished at a substantially constant temperature $T_R$, from $P_B$ to $P_{opn}$ (i.e. from point A to point B in the diagram FIG. 4). Next, the temperature of the liquid refrigerant 44 is decreased in the cold inlet line 32 by the refrigerator 36, while pressure on the liquid refrigerant 44 is maintained substantially constant at $P_{opn}$. This decrease is from the essentially environmental temperature $T_R$ to the operational cryoablation temperature $T_{min}$. In FIGS. 4 and 1, this is represented as a change from point B ($T_R$, $P_{opn}$) to point C ($T_{min}$, $P_{opn}$). With liquid refrigerant 44 under the conditions of point C ($T_{min}$, $P_{opn}$), it passes through the cryotip 22 for the purpose of performing a cryosurgical procedure.

During a cryosurgical procedure, the cryotip 22 is positioned against the tissue (not shown) that is to be cryoablated. As a consequence of heat transfer from the tissue, the cryosurgical procedure will cause the liquid refrigerant 44 to warm inside the cryotip 22. Despite this warming, it can happen that the cryotip 22 will adhere (i.e. freeze) to the tissue. When this happens, in order to overcome any adhesion that may have been established between the cryotip 22 and tissue, the system 10 may provide for additional warming of the cryotip 22 after the cryosurgical procedure has been completed. Specifically, this additional warming is provided by a heat exchanger 56 that is integrated into the cold inlet line 32 of the system 10, substantially as shown in FIG. 3.

Functionally, the amount of additional warming of the liquid refrigerant 44 provided by the heat exchanger 56 can be controlled by a concerted operation of the respective slide valves 58 and 62. For example, at the operational extremes, a cryosurgical procedure would likely be accomplished with slide valve 58 open, and slide valve 62 closed. On the other hand, the refrigerator 36 can be completely by-passed when the slide valve 58 is closed and the slide valve 62 is open. As will be appreciated by the skilled artisan, selective operation of the valves 58 and 62 will provide a warmer liquid refrigerant 44 for the cryotip 22, as desired. In any event, FIG. 4 indicates that the liquid refrigerant 44 is warmed to a nominal temperature $T_P$ while passing through the cryotip 22 (i.e. liquid refrigerant 44 moves from point C to point D in FIG. 4). Subsequently, after the liquid refrigerant 44 leaves the cryotip 22 it passes through a heat exchanger 40 where it is warmed to the environmental temperature $T_R$ (i.e. point E in FIG. 4). A check valve 42 then returns the pressure on the liquid refrigerant 44 to the pressure $P_B$ for its return to the container 12 (see point F in FIG. 4). The liquid refrigerant 44 can then be recycled as desired.

While the particular Method and System for Cryoablation Treatment as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for cryoablating tissue which comprises the steps of:
   providing a closed loop system having a container for holding a liquid refrigerant at a base pressure $P_B$ and an environmental temperature $T_R$, a liquid pump for moving the liquid refrigerant from the container and through the system at an elevated operational pressure $P_{opn}$, a refrigerator for receiving the liquid refrigerant from the pump and for cooling the liquid refrigerant to a temperature $T_{min}$ at the operational pressure, a cryoprobe for receiving the liquid refrigerant from the refrigerator for use in a cryoablation procedure, and a return line for returning liquid refrigerant as a liquid from the cryoprobe to the container, wherein the base pressure $P_B$ is in a range of approximately 0.3 MPa to 1.5 MPa, wherein $T_{min}$ is less than approximately −100° C., and wherein $P_{opn}$ is in a range of approximately 0.3 MPa to 5.0 MPa;
   positioning the cryoprobe against the tissue;
   operating the liquid pump to move the liquid refrigerant through the system for cryoablation of the tissue; and
   cycling the liquid refrigerant as a liquid from the container and through the system.

2. A method as recited in claim 1 wherein the refrigerator comprises:
   a pressure vessel for holding a liquid cryogen; and
   a tube having a coiled portion, wherein the tube connects the container in fluid communication with the cryoprobe and the coiled portion is submerged in the liquid cryogen.

3. A method as recited in claim 2 wherein the system further comprises a heater for receiving a portion of the liquid refrigerant from the pump, and for heating the portion of liquid refrigerant for direct transfer to the cryoprobe, a first slide valve for controlling the flow of liquid refrigerant from the pump to the refrigerator, and a second slide valve for controlling the flow of liquid refrigerant from the pump to the heater, and the method further comprises the step of coordinating operation of the first and second slide valves to establish a predetermined temperature $T_P$ for liquid refrigerant in the cryoprobe, wherein $T_P$ is equal to or greater than $T_R$.

* * * * *